(12) United States Patent
Folkvord et al.

(10) Patent No.: US 9,560,887 B2
(45) Date of Patent: Feb. 7, 2017

(54) FLUID MANAGEMENT DEVICE FOR EXERCISING ATHLETES

(71) Applicant: Dean Folkvord, Three Forks, MT (US)

(72) Inventors: Dean Folkvord, Three Forks, MT (US); David Yakos, Bozeman, MT (US); Stephen Sanford, Bozeman, MT (US); Joel Switzer, Bozeman, MT (US)

(73) Assignee: Folkvord Products, LLC, Three Forks, MT (US)

( * ) Notice: Subject to any disclaimer, the term of this patent is extended or adjusted under 35 U.S.C. 154(b) by 349 days.

(21) Appl. No.: 14/203,848

(22) Filed: Mar. 11, 2014

(65) Prior Publication Data
US 2015/0258355 A1    Sep. 17, 2015

(51) Int. Cl.
*A61M 16/10* (2006.01)
*A62B 7/10* (2006.01)
*A41D 13/11* (2006.01)

(52) U.S. Cl.
CPC .............. *A41D 13/11* (2013.01); *A61M 16/10* (2013.01); *A62B 7/10* (2013.01)

(58) Field of Classification Search
CPC ....... A62B 23/00; A62B 23/02; A62B 23/025; A62B 23/06; A61M 16/10; A61M 16/105; A61M 16/106; A61M 16/107; A61M 16/06; A61M 16/047
See application file for complete search history.

(56) References Cited

U.S. PATENT DOCUMENTS

| 2,895,472 | A | * | 7/1959 | Matheson | .............. | A62B 23/02 128/206.15 |
|---|---|---|---|---|---|---|
| 3,072,119 | A | * | 1/1963 | Matheson | .............. | A62B 23/02 128/206.17 |
| 4,098,270 | A | | 7/1978 | Dolby | | |
| 4,196,728 | A | * | 4/1980 | Granite | .............. | A61M 16/1045 128/201.13 |
| 4,231,364 | A | | 11/1980 | Speshyock | | |
| D325,780 | S | | 4/1992 | Policappelli | | |
| 5,295,478 | A | * | 3/1994 | Baldwin | .......... | A61M 16/0048 128/202.28 |
| 5,325,892 | A | * | 7/1994 | Japuntich | ............. | A62B 18/025 137/855 |
| 5,438,981 | A | * | 8/1995 | Starr | ........................ | A62B 7/12 128/205.24 |
| 5,771,885 | A | * | 6/1998 | Putrello | .................. | A62B 23/02 128/205.27 |
| 5,937,856 | A | * | 8/1999 | Jonasson | ........... | A61M 16/1045 128/200.24 |

(Continued)

*Primary Examiner* — Valerie L Woodward
*Assistant Examiner* — Michael Tsai
(74) *Attorney, Agent, or Firm* — Antoinette M. Tease

(57) ABSTRACT

A fluid management device comprising an air filler assembly comprising a filter, a body, a mouthpiece and a flap valve, and a fluid deflector situated between the filter and the mouthpiece. The body comprises condensation collection guide channels located on an inside surface of the body behind the fluid deflector that direct condensation and saliva into a collection basin located behind the fluid deflector at a base of the fluid deflector. The first end of the flap valve is attached to the body, and the second end of the flap valve is situated directly beneath the collection basin. When the flap valve is in an open position, fluids collected in the collection basin escape from the device by dripping out of it.

10 Claims, 15 Drawing Sheets

(56) References Cited

U.S. PATENT DOCUMENTS

| | | | |
|---|---|---|---|
| 6,966,318 B1* | 11/2005 | Tsuug | A62B 23/06 128/206.11 |
| 7,025,060 B1 | 4/2006 | Nicholson | |
| D569,499 S | 5/2008 | McCullough | |
| 8,397,726 B2 | 3/2013 | Evensson | |
| 2004/0007234 A1 | 1/2004 | Duxbury | |
| 2006/0081249 A1 | 4/2006 | Duxbury | |
| 2006/0137689 A1 | 6/2006 | Evensson | |
| 2010/0059060 A1 | 3/2010 | Evensson | |
| 2014/0305431 A1* | 10/2014 | Holley | A61M 16/085 128/201.13 |

* cited by examiner

US 9,560,887 B2

FLUID MANAGEMENT DEVICE FOR EXERCISING ATHLETES

BACKGROUND OF THE INVENTION

1. Field of the Invention

The present invention relates generally to the field of air filters, and more specifically, to a portable and lightweight fluid (air and liquid) management device that can be worn by athletes while exercising and without restricting performance. This device serves the dual function of filtering the air and expelling moisture (saliva) from the device to increase the longevity and functionality of the filter. Although specifically designed for athletes, the device can be worn by any individuals who live or work in geographic areas where the air quality is poor.

2. Description of the Related Art

Athletes often exercise in urban environments where air quality is poor. When exercising, these athletes may inhale air contaminated by vehicle, industrial and urban exhaust. An exercising body typically takes in up to thirty (30) times more air than one at rest. In situations involving athletic exertion in areas of poor air quality, the inhalation of undesirable substances may counteract any health benefits derived by the act of exercising. Furthermore, most people generate some amount of saliva during exercise. The present invention is specifically designed to ensure that the air filter remains dry by collecting and expelling ah moisture from the device.

Although, designed specifically for use by athletes, the present invention is not limited to use by such persons. In fact, many residents of urban areas wear dust masks to reduce the amount of contaminants inhaled. The present invention may be used by both athletes and non-athletes who live or work in areas with poor air quality.

The prior art includes various examples of air filters and air filtration systems, but none of these devices is designed specifically to fit into the mouth of an athlete while exercising and to collect and dispel saliva generated by the athlete during exercise. As is evident from the following discussion of the prior art, the devices already in existence are, for the most part, air intake management systems. The present invention is a significant improvement to these devices because it keeps the filter dry by collecting and expelling all moisture from the device.

U.S. Pat. No. 4,098,270 (Dolby, 1978) discloses a smoke mask comprising a mouthpiece, a face shield that covers the wearer's nose and eyes, and a replaceable air filtration cartridge system attached to the face shield. This apparatus could not be worn by an athlete while exercising because it covers the eyes, nose and mouth.

U.S. Pat. No. 4,231,364 (Speshyock, 1980) provides a respiratory control system comprising a mouthpiece with a centrally located filtering cartridge and valve means for controlling the flow of air past the filtering material upon inhalation and out a separate corridor on exhalation. This particular device does not incorporate any system for managing saliva.

U.S. Pat. No. 5,771,385 (Futrello, 1998) describes an exercise filter that is worn in the mouth. The exercise filter comprises two filters and two one-way valves. This device does not incorporate any system for managing saliva.

U.S. Pat. No. 7,025,060 (Nicholson) discloses a personal air filtration device, held in the mouth, that is comprised of a cylindrical exhalation tube with a filter media housing that is arranged concentrically around the periphery of the exhalation tube. This device does not incorporate any system for managing saliva.

U.S. Pat. No. 8,397,726 (Evensson, 2013) provides a breathing protective device, also held in the mouth, that is comprised of a tubular elongated filter housing and a mouthpiece with an air canal. The filter is arranged to separate a first space from a second space, and the air canal is arranged to enable the supply of inhalation air from the first space (via the filter) and the escape of exhalation air from the second space. Like the other prior art devices referenced above, this device does not incorporate any system for managing saliva.

U.S. Pat. No. D569,499 (McCullough, 2008) and D325,780 (Policappelli, 1992) are design patents for a cough silencer and a combined respirator mouthpiece and filter, respectively. Neither of these designs is structurally similar to the present invention.

U.S. Patent Application Pub. Nos. 2004/0007234 (Duxbury) and 2006/0081249 (Duxbury) both describe a personal respirator, supported in the mouth, comprised of a hollow connector with an air filtration end and an air mouthpiece end and an air-permeable filter that seals the first air filtration end. The air mouthpiece end forms an airtight seal when held anterior to the teeth between the lips of the wearer. This device does not incorporate a saliva management system.

U.S. Patent Application Pub. No. 2006/0137689 (Evensson) discloses a breathing protective device comprised of a mouthpiece and a filter house with a filter house chamber and a first wall section with a number of through holes. A filter is located inside of the first wall section of the filter house chamber. The filter house is elongated and extends longitudinally. This device does not incorporate a saliva management system.

BRIEF SUMMARY OF THE INVENTION

The present invention is a fluid management device comprising: an air filter assembly comprising a filter, a body, a mouthpiece and a flap valve; and a fluid deflector situated between the filter and the mouthpiece; wherein the body comprises condensation collection guide channels located on an inside surface of the body behind the fluid deflector; wherein the fluid collection guide channels direct condensation and saliva into a collection basin located behind the fluid deflector at a base of the fluid deflector; wherein the flap valve comprises a first end and a second end, the first end being attached to the body, and the second end being situated directly beneath the collection basin; and wherein when the flap valve is in an open position, it allows fluids collected in the collection basin to escape from the device by dripping out of it. In a preferred embodiment, the body comprises a filter orifice situated on a front side of the body, the filter comprises filter media and a frame, and the frame fits inside of the filter orifice.

In a preferred embodiment, the filter orifice comprises at least one filter positive stop on an interior of the filter orifice, and the filter positive stop prevents the filter from coming into contact with the fluid deflector. In another preferred embodiment, the fluid deflector comprises a filter positive stop on a front surface of the fluid deflector, and the filter positive stop prevents the filter from coming into contact with the fluid deflector.

In one embodiment, the fluid deflector is a rigid and stationary plastic shield that is fixedly attached to a bottom of the filter orifice. In an alternate embodiment, the fluid deflector is comprised of a flexible material that allows the fluid deflector to flex downward during inhalation and upward during exhalation. In another alternate embodiment the fluid defector comprises a hinge spring that allows the fluid deflector to flex downward during inhalation and upward during exhalation.

In a preferred embodiment, the device further comprises a flap valve support structure that is integral to the body and that lies between the flap valve and the fluid deflector. Preferably, the fluid collection guide channels are located on either side of the flap valve support structure. In all embodiments, the fluid deflector preferably comprises a front-facing convex surface and a rear-facing concave surface.

BRIEF DESCRIPTION OF TOE DRAWINGS

FIG. 10B is a detail view of the spring attachment slot.

REFERENCE NUMBERS

Figure 1:
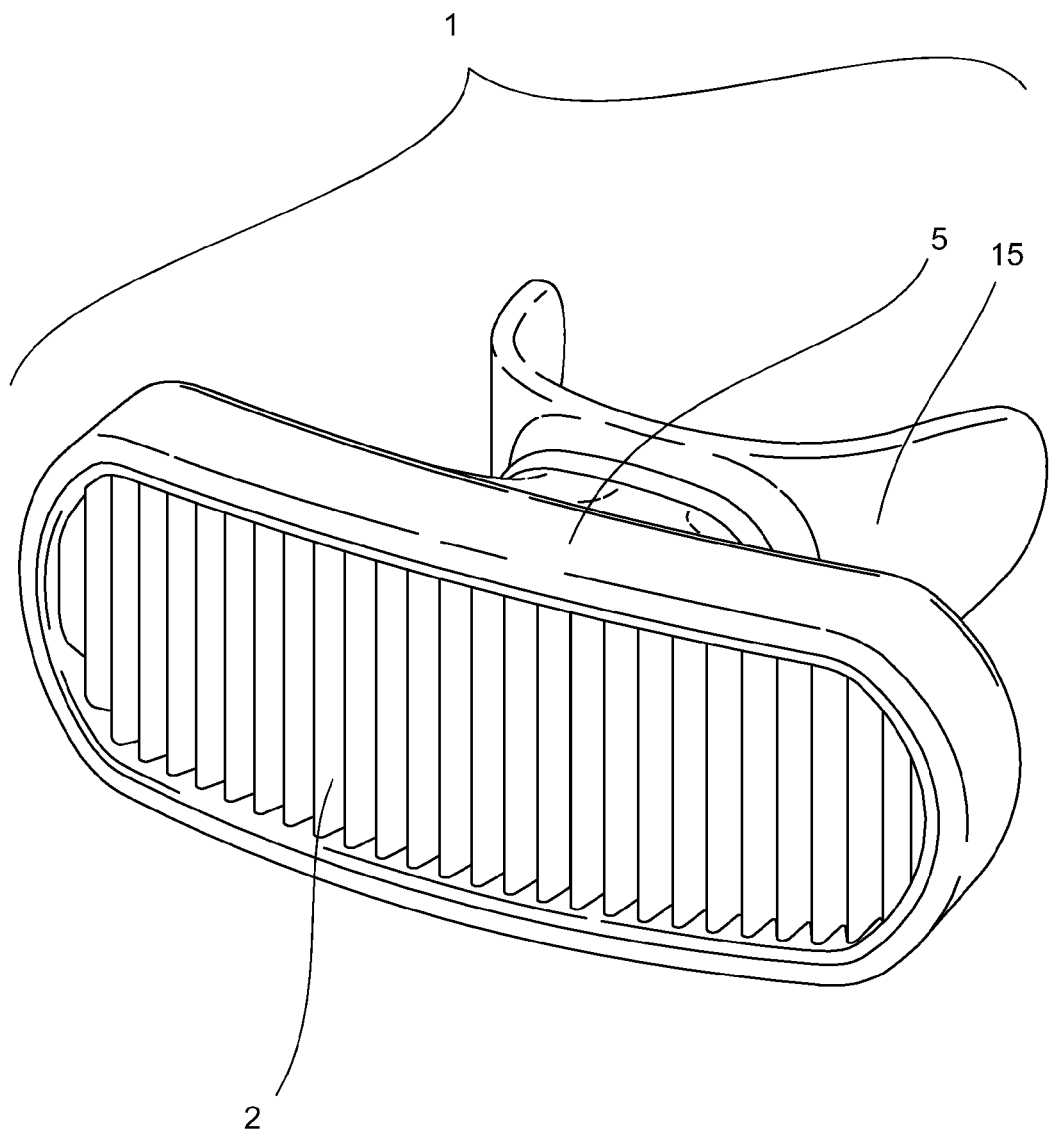
FIG. 1 is a front perspective view of a first embodiment of the present invention.

1 Air filter assembly
2 Filter
3 Frame
4 Filter media
5 Body
5a Mouth orifice
5b Filter orifice
6 Filter positive stop
7 Mouthpiece attachment groove
8 Fluid deflector
9 Moisture collection basin
10 Flap valve support structure
10a Support structure opening
11 Condensation collection guide channels
12 Flan valve
13 Adhesive interface
14 Air seal interface
15 Mouthpiece
16 Mouthpiece attachment lip
17 First alternate embodiment (with flexible fluid deflector)
18 Flexible fluid deflector
19 Adhesive interface
20 Second alternate embodiment (with hinged fluid deflector)
20a Hinged fluid deflector
21 Hinge base wing
22 Hinge deflector wing
23 Hinge pivot pin
24 Hinge spring
25 Spring attachment slot
26 Air flow inhale
27 Air flow exhale

DETAILED DESCRIPTION OF INVENTION

Typical air filtration systems worn by athletes collect moisture in the filter while the athlete is exercising. This moisture may come from the air being inhaled or from the athlete himself in the form of saliva present in the exhaled air. If the filter is being used by a runner, for example, the fiber might get wet, freeze and crack or clog. In these situations, the efficacy of the filter is diminished.

The present invention combines an air management system with a liquid (moisture/saliva) management system. The internal geometry of the present invention comprises fluid deflectors that direct the exhaled fluid (carbon dioxide and saliva) through a flap valve and into a collection basin. The flow channels of the present invention encourage condensation present in the exhaled air to drop downward toward the collection basin, which is located at the lowest point of the device (behind the fluid deflector at the base of the fluid deflector). All saliva exhaled by the wearer is collected in this basin. With each exhalation, a flap valve opens up and allows the saliva to drip out of the device.

The present invention encompasses three different embodiments of the fluid deflector. In one embodiment, the fluid deflector is a stationary, rigid plastic ridge. In another embodiment, the fluid deflector is a rubbery (flexible) flap. In a third embodiment, the fluid deflector is on a hinge, which allows the fluid deflector to move. The first of these embodiments is most likely the easiest to manufacture, but the second and third of these embodiments may allow for better air flow because the fluid deflectors are allowed some degree of movement.

Unlike the prior art, the present invention captures and manages saliva with fluid deflectors, fluid guide channels, a moisture collection basin, and a fluid release that is activated upon exhalation. These and other structural features of the present invention are discussed more fully below with reference to the figures.

FIG. 1 is a front perspective view of the present invention. As shown in this figure, the air filter assembly 1 comprises a filter 2, a body 5, and a mouthpiece 15. All three of the embodiments described herein comprise these three components. As shown in subsequent figures, the embodiments differ in terms of the configuration of the fluid deflectors 8 (not shown) located inside of the body 5.

Figure 2:
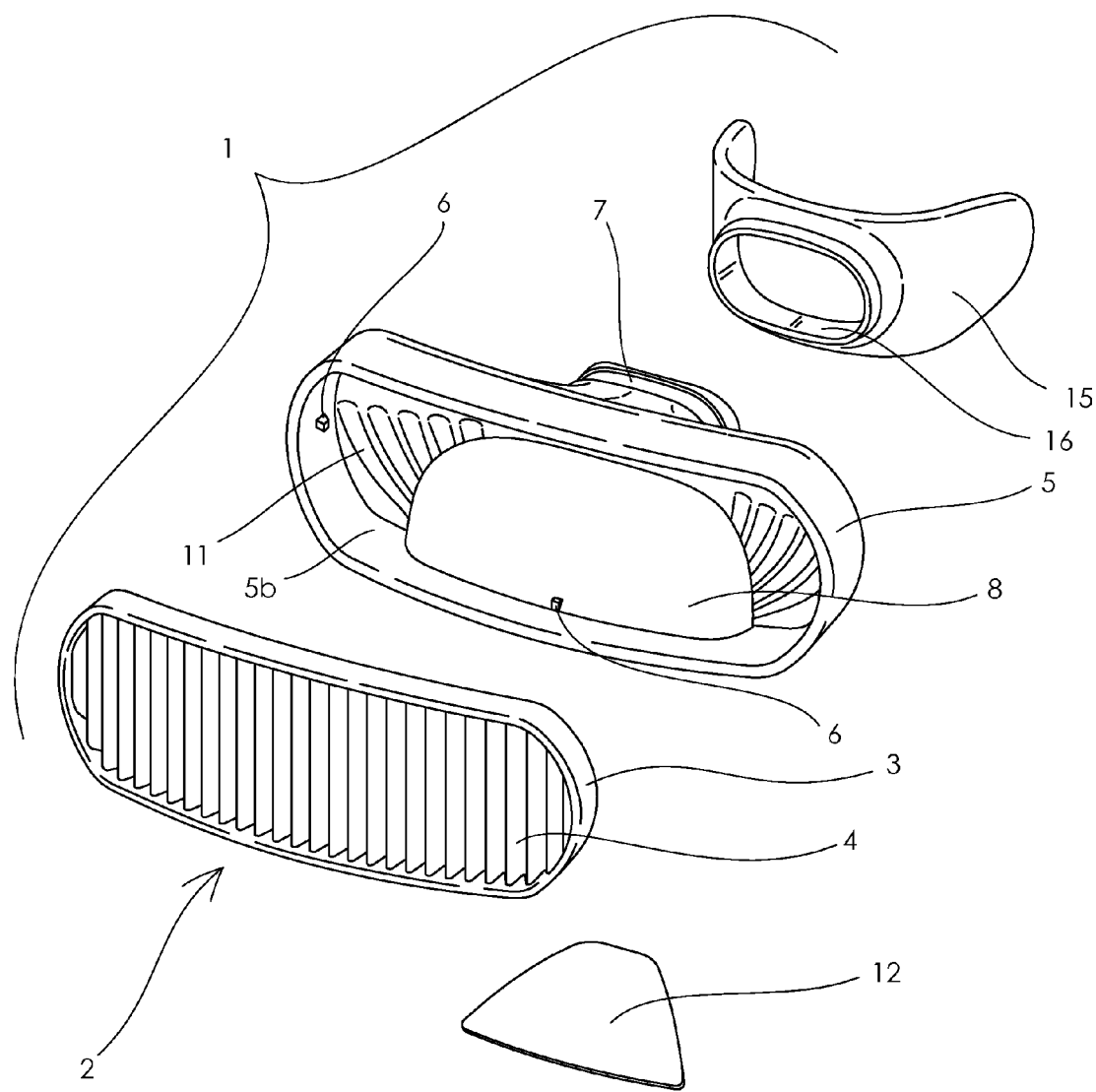
FIG. 2 is an exploded view of a first embodiment of the present invention.

FIG. 2 is an exploded view of a first embodiment of the present invention. As shown in this figure, the filter 2 comprises filter media 4 situated inside of a frame 3. The frame 3 fits inside of the filter orifice 5b on the front side of the body 5. Filter positive stops 6 on the interior of the filter orifice 5*b* (although only one fitter positive stop 6 is visible in this figure, there is a filter positive stop 6 on either side of the filter orifice 5*b*) and on the bottom of the fluid deflector 8 prevent the filter 2 from coming into contact with the fluid deflector 8.

In this embodiment, the fluid deflector 8 is in the form of a rigid and stationary plastic deflector or shield, the bottom of which is fixedly attached to the bottom of the filter orifice 5*b*. Condensation collection (or fluid) guide channels 11 are located inside of the body 5 behind the fluid deflector 8. The mouthpiece 15 attaches to the rear end of the body 5 via a mouthpiece attachment groove 7 (on the rear end of the body 5) that is coupled to the mouthpiece attachment lip 16 ion the mouthpiece 15). This is shown more clearly in FIG. 3.

Figure 5:
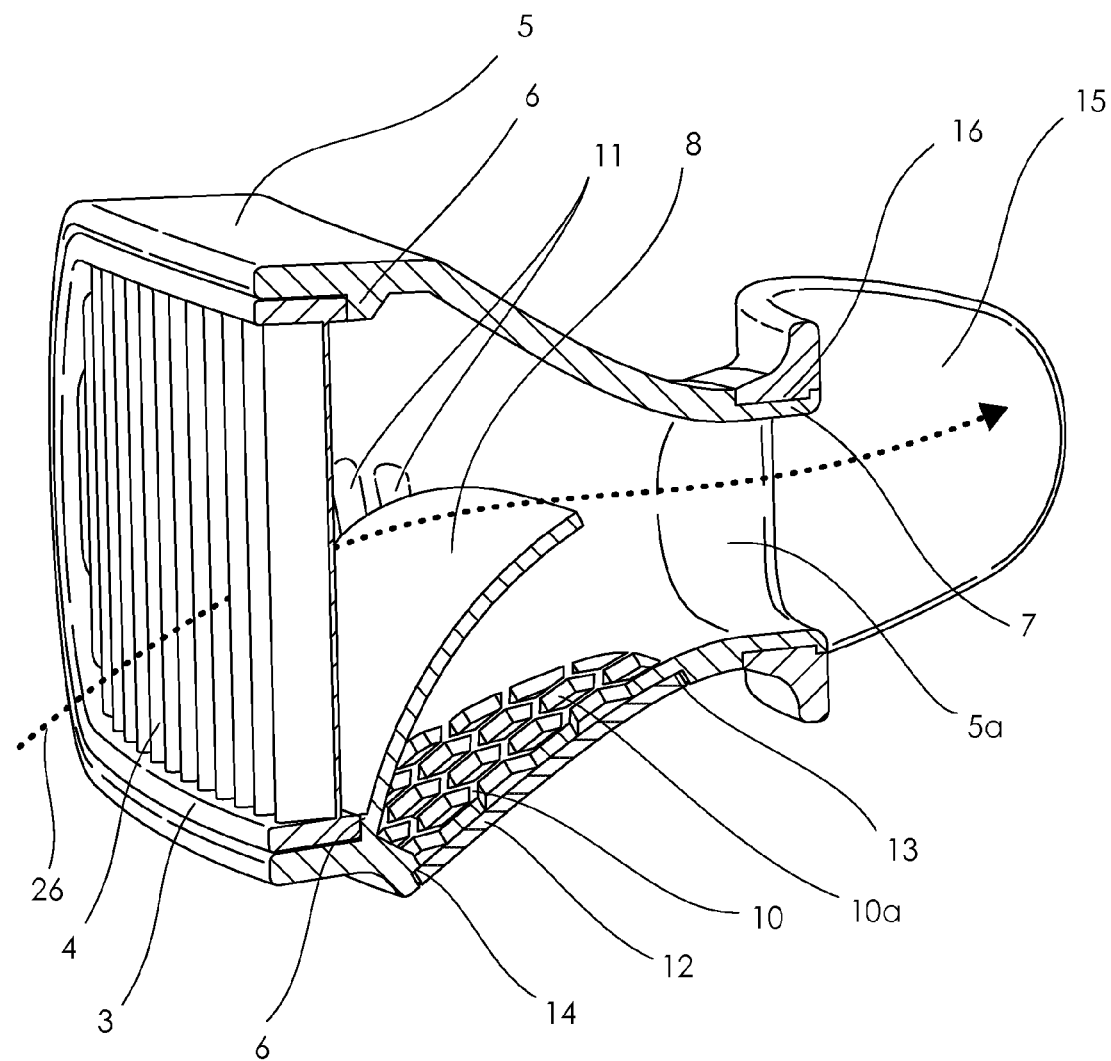
FIG. 5 is a side cross-section view of a first embodiment of the present invention shown in an inhalation state.
Figure 6:
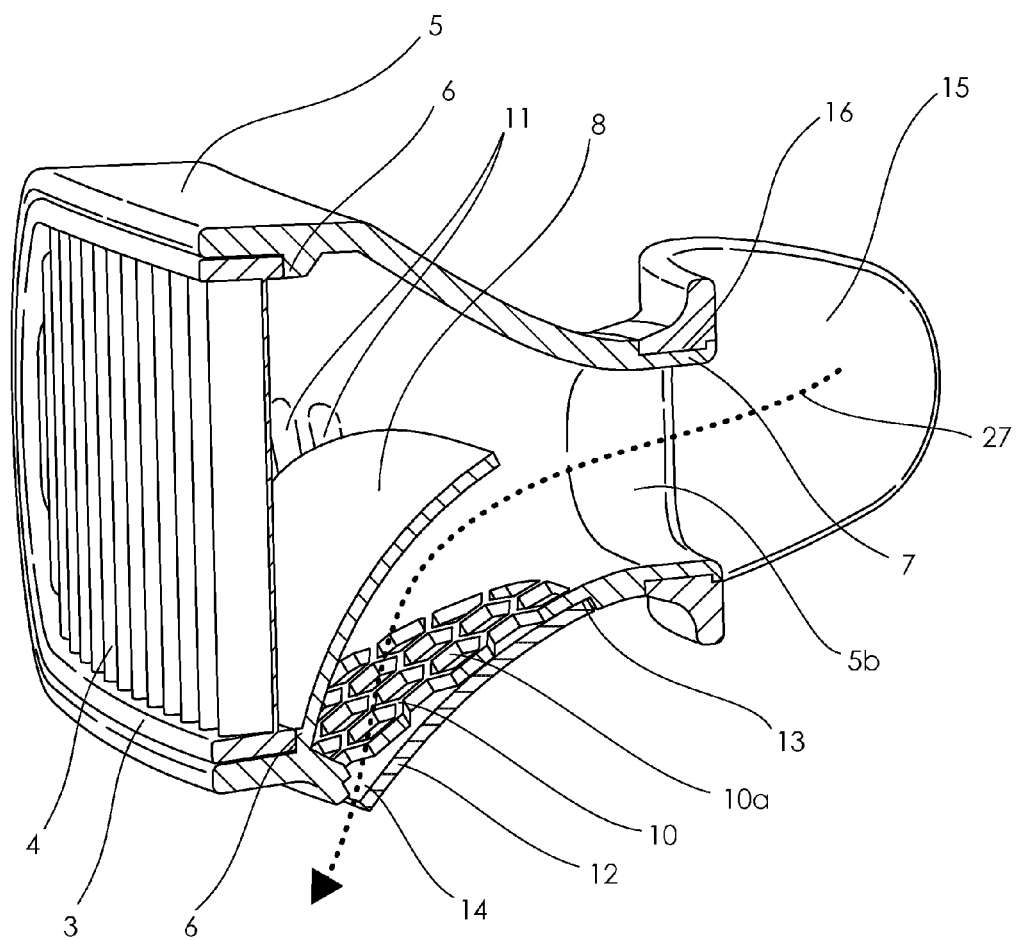
FIG. 6 is a side cross-section view of a first embodiment of the present invention shown in an exhalation state.

The air filter assembly 1 further comprises a flap valve 12, the location and operation of which is shown and described more fully in connection with FIGS. 5 and 6 (first embodiment), 8 and 9 (second embodiment), and 11 and 12 (third embodiment). When the flap valve 12 is in an open position, it allows the moisture collected in the collection basin 9 to escape (see FIGS. 6, 9 and 12).

Figure 2A:
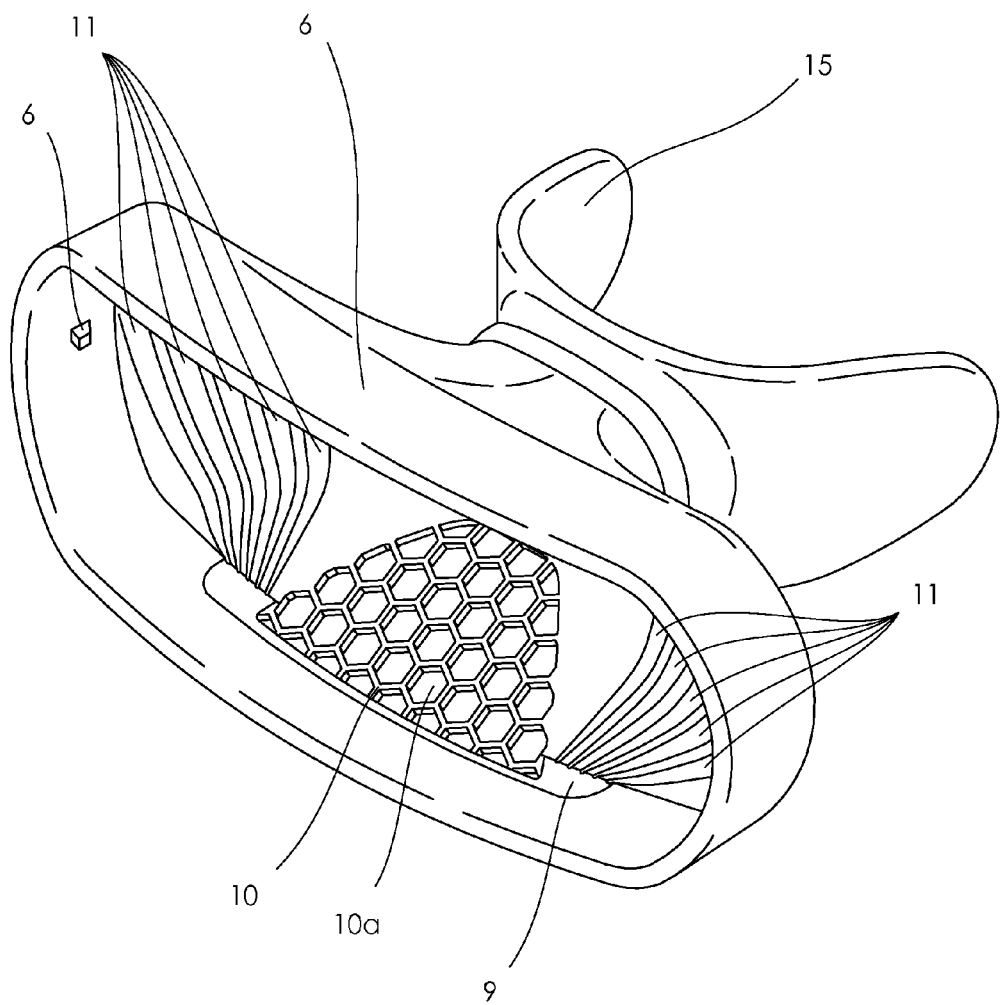
FIG. 2A is a front perspective view of a first embodiment of the present invention shown without the filter and fluid deflector.

FIG. 2A is a front perspective view of a first embodiment of the present invention shown without the filter and fluid deflector. As shown in this figure, the condensation collection guide channels 11 extend all the way to the collection basin 9 located at the bottom of the body 5 surrounding the filter frame 3 (not shown). Thus, the condensation collection guide channels 11 serve to direct any condensation or fluid that collects inside the device to the collection basin 9. This figure also shows the flap valve support structure 10 (comprised of a plurality of support structure openings 10*a*), the terminal end of which is situated directly underneath the collection basin 9.

Figure 3:
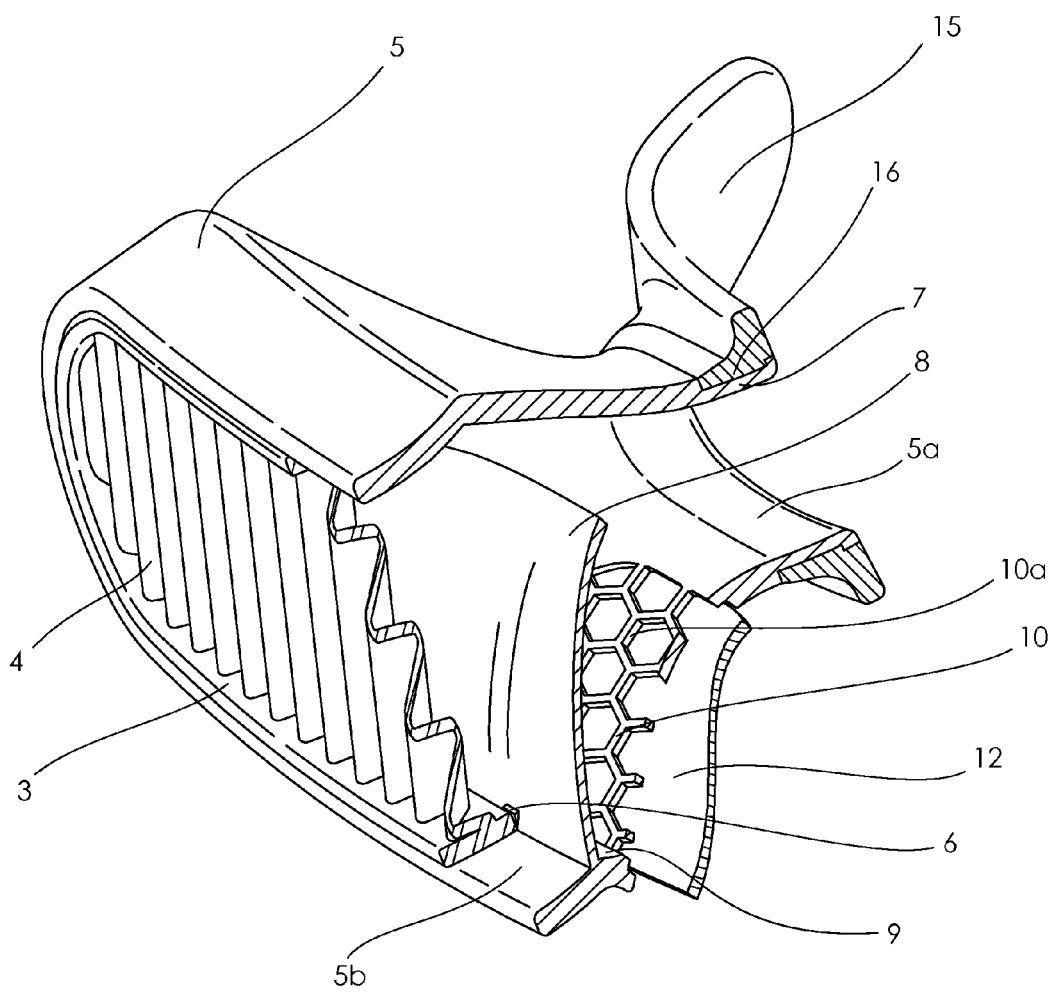
FIG. 3 is a first cutaway view of a first embodiment of the present invention.

FIG. 3 is a first cutaway view of a first embodiment of the present invention. As shown in this figure, the fluid deflector 8 is situated behind the filter media 4 between the filter media 4 and the flap valve support structure 19. The purpose of the flap valve support structure 10 is to keep the flap valve 12 from being sucked up into the device during inhalation. Although shown here as a honeycomb structure, the flap valve support structure could take the form of a mesh or grill structure. The flap valve 12 is preferably constructed of a material (such as rubber or thermoplastic elastomer) that will retain its shape when no force is applied to it (i.e., that is sufficiently rigid to overcome gravity) but that will bend when pressure (in the form of exhaled air) is applied to it. Preferably, the flap valve 12 is glued or over-molded to the mouth orifice 5*a* (see also FIG. 4A) so that it sits flat against the flap valve support structure 10 when in a closed position.

The mouth orifice 5*a* on the rear end of the body 5 forms a passageway for inhalation and exhalation when the body 5 is attached to the mouthpiece 15. Note that the mouthpiece attachment lip 16 fits into the mouthpiece attachment groove 7 to secure the mouthpiece 15 on the body 5.

Figure 4:
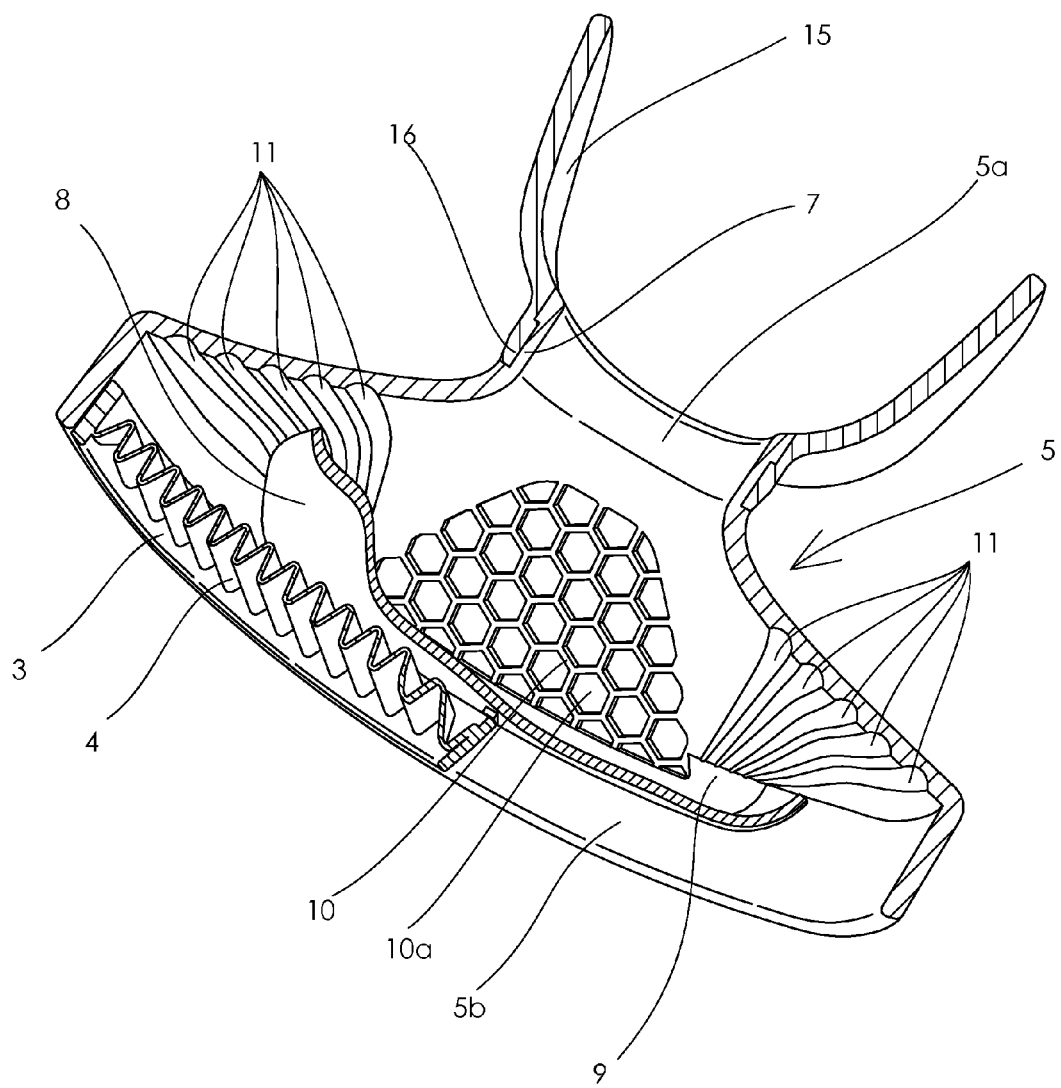
FIG. 4 is second cutaway view of a first embodiment of the present invention.

FIG. 4 is second, cutaway view of a first embodiment, of the present invention. For references purposes, the dotted line in FIG. 7 indicates where this cross-section was taken (a portion of the fluid deflector 8 has been additionally cut away to show the collection basin 9). Note that the interior of the body 5 preferably comprises a plurality of fluid collection guide channels 11. These channels 11 are situated on either side of the flap valve support structure 10 and terminate at the collection basin 9. As noted above, the purpose of these channels 11 is to direct fluid (in the form of condensation or saliva) downward toward the collection basin 9.

Figure 4A:
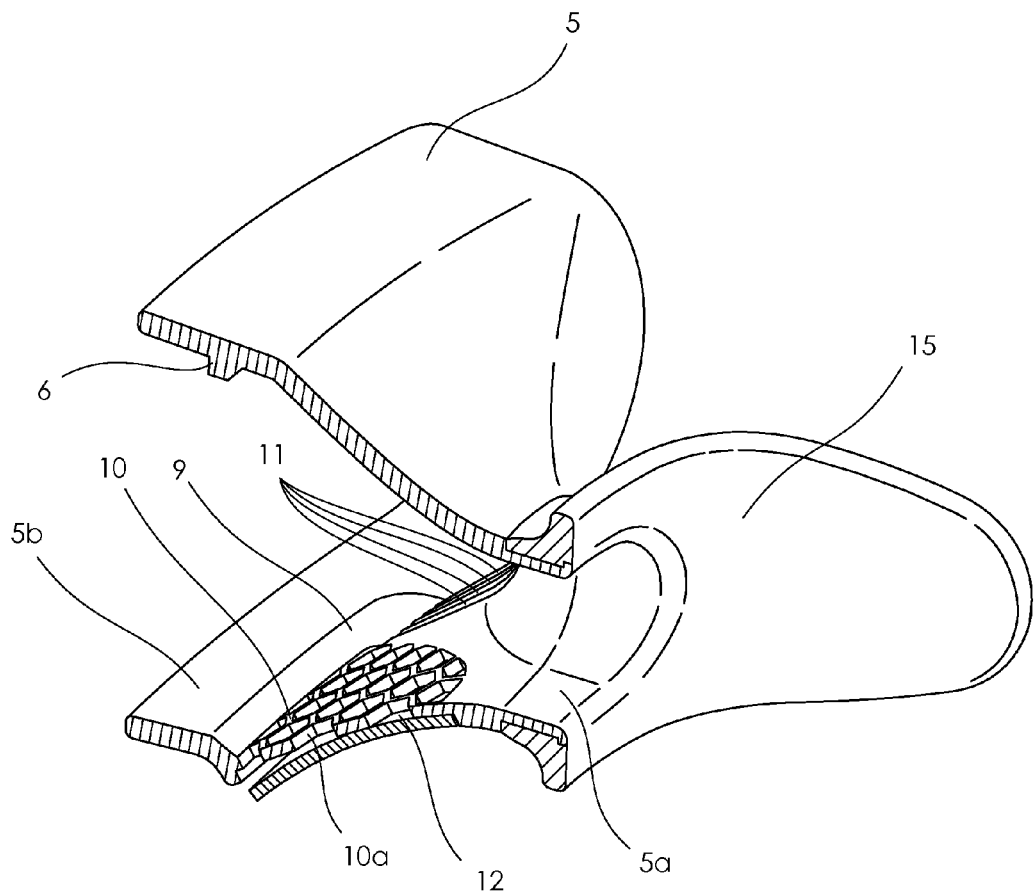
FIG. 4A is a rear perspective cutaway view of a first embodiment of the present invention.

FIG. 4A is a rear perspective cutaway view of a first embodiment of the present invention. This figure shows that the condensation collection guide channels 11 terminate in the collection basin 9. It also shows that the proximal (upper) end of the flap valve support structure 10 is preferably integral with or connected to the lower surface of the mouth orifice 5A, and the terminal end of the flap valve support structure 10 is situated directly beneath the collection basin 9, as noted above. In this figure, the flap valve 12 is shown in an open position, which allows the fluid that has been collected in the collection basin 9 to escape from the device by dripping out through the flap valve support structure 10 between the collection basin 9 and the terminal end of the flap valve 12.

FIG. 5 is a side cross-section view of a first embodiment of the present invention shown in an inhalation state. In this figure, the direction of air flow during inhalation is indicated by reference number 26. During inhalation, air enters through the front of the filter 2, passes through the filter 2, and then travels over the top of the fluid deflector 8 and through the mouth orifice 5*a* into the wearer's mouth. Note that the front-facing surface of the fluid deflector 8 is preferably arcuate (or bow-shaped). This arcuate surface directs the inhaled air over the fop of the fluid deflector 8. In this embodiment, the height of the fluid deflector 8, which is stationary and does not move, extends from the bottom of the fluid deflector 8 (which is on approximately the same horizontal plane as the bottom of the filter 2) to roughly the center of the filter 2. This shape allows inhaled air to pass over the top of the fluid deflector shield 8 but also enables the fluid deflector 8 to trap and redirect exhaled air downward (see FIG. 6).

FIG. 6 is a side cross-section view of a first embodiment of the present invention shown in an exhalation state. On exhalation, air passes through the mouth orifice 5*a* and bits the rear-facing concave side of the fluid deflector 8. The fluid deflector 8 deflects the exhaled air downward through the openings 10*a* in the flap valve support structure 10 and onto the flap valve 12. This downward pressure of the exhaled air on the flap valve 12 causes the flap valve 12 to bend downward and the air seal interlace 14 to open, thereby allowing the exhaled air to escape from the device, as indicated by the arrow 27. Once the exhaled air has exited the device, the flap valve 12 springs back into the position shown in FIG. 7, with the air seal interface 14 in a closed position.

Any saliva that is contained in the exhaled air would also hit the rear-facing concave surface of the fluid deflector 8 and be deflected downward into the collection basin 9. When the air seal interface 14 opens, the saliva that has been collected in the collection basin 9 drips downward and exits the device through the (now open) air seal interface 14 free also FIG. 4A).

Figure 7:
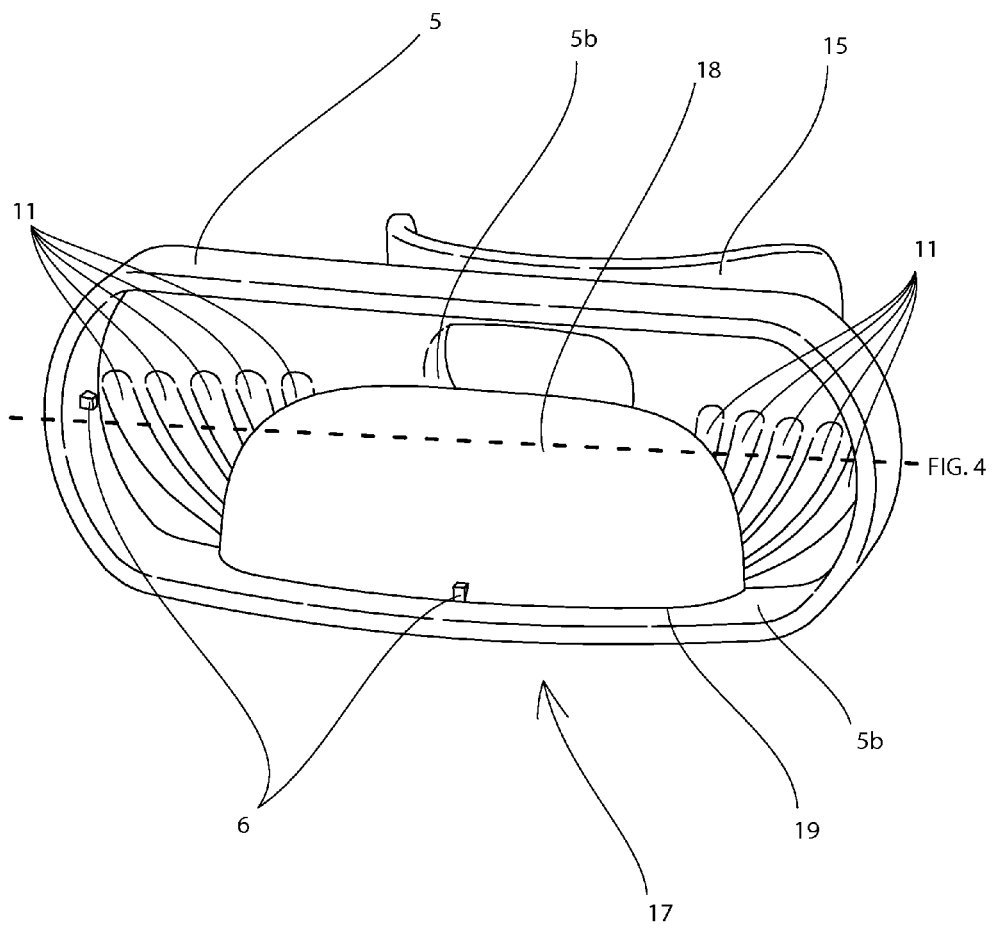
FIG. 7 is a perspective view of a second embodiment of the present invention shown without the filter.

FIG. 7 is a perspective view of a second embodiment of the present invention shown without the filter. This figure shows an alternate embodiment 17 in which the fluid deflector 18 takes a different form than that shown in the previous figures. In this embodiment, the fluid deflector 18 is comprised of rubber or a similarly flexible material. The fluid deflector 18 has the same front-facing convex and rear-facing concave surfaces as in the previous embodiment, but the height of the fluid deflector 18 at rest is less than in the previous embodiment. This is because the fluid deflector flexes upward during exhalation, which allows it to capture at least as much of the exhaled air and saliva as in the previous embodiment.

Figure 8:
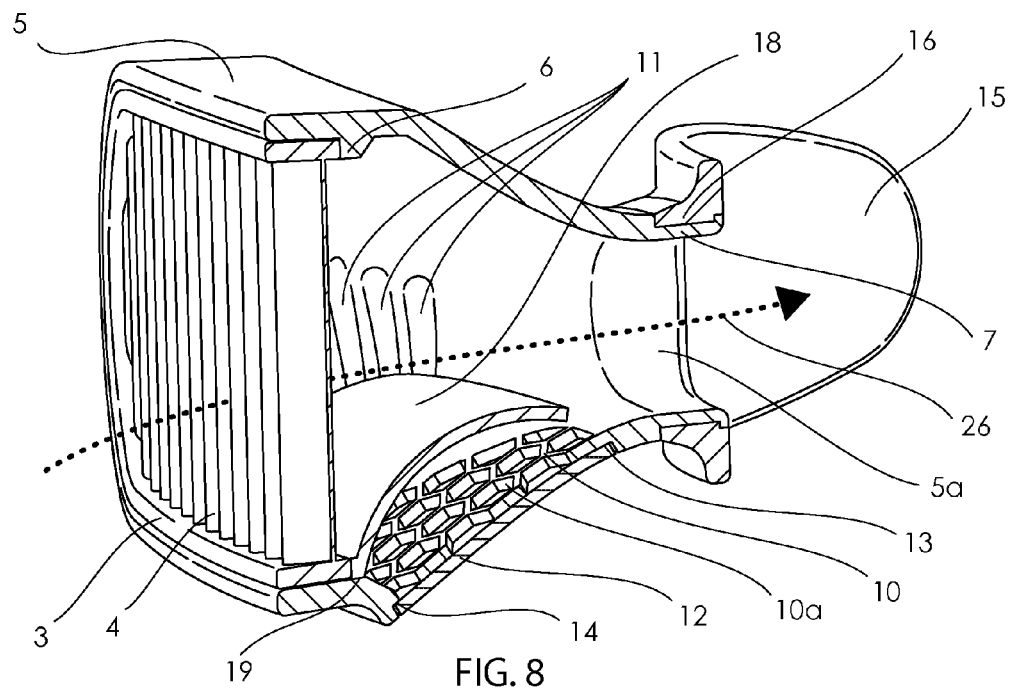
FIG. 8 is a side cross-section view of a second embodiment of the present invention shown in an inhalation state.
Figure 9:
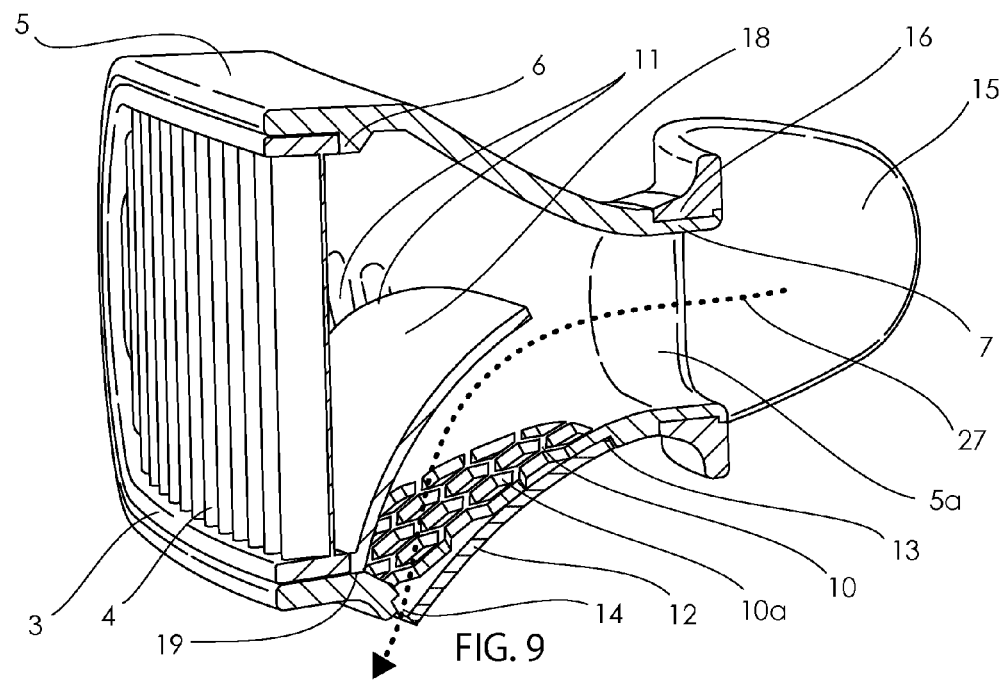
FIG. 9 is a side cross-section view of a second embodiment of the present invention shown in an exhalation state.

FIG. 8 is a side cross-section view of a second embodiment of the present invention shown in an inhalation state, and FIG. 9 is a side cross-section view of a second embodiment of the present invention shown in an exhalation state. As shown in FIG. 8, the inhaled air forces the top of the fluid deflector 8 downward. As shown in FIG. 9, the exhaled air hitting the rear-facing concave surface of the fluid deflector 18 causes the fluid deflector 18 to extend upward. This upward and downward flexing of the fluid deflector 18 likely increases the efficacy of the device by providing a straighter (and greater) path of ingress for the inhaled air and allowing less exhaled air to escape over the top of the fluid deflector 18. The purpose of the fluid deflector 18 is to capture as much exhaled air and saliva as possible and prevent any exhaled air and saliva from traveling back through the filter 2.

In the embodiment shown in FIGS. 7-9, the fluid deflector 18 is attached to the frame 5 via an adhesive interface 19. Note that in the previous embodiment, the fluid deflector 8 is part of the same injection-molded piece as the frame 5 (see FIG. 5).

Figure 10:
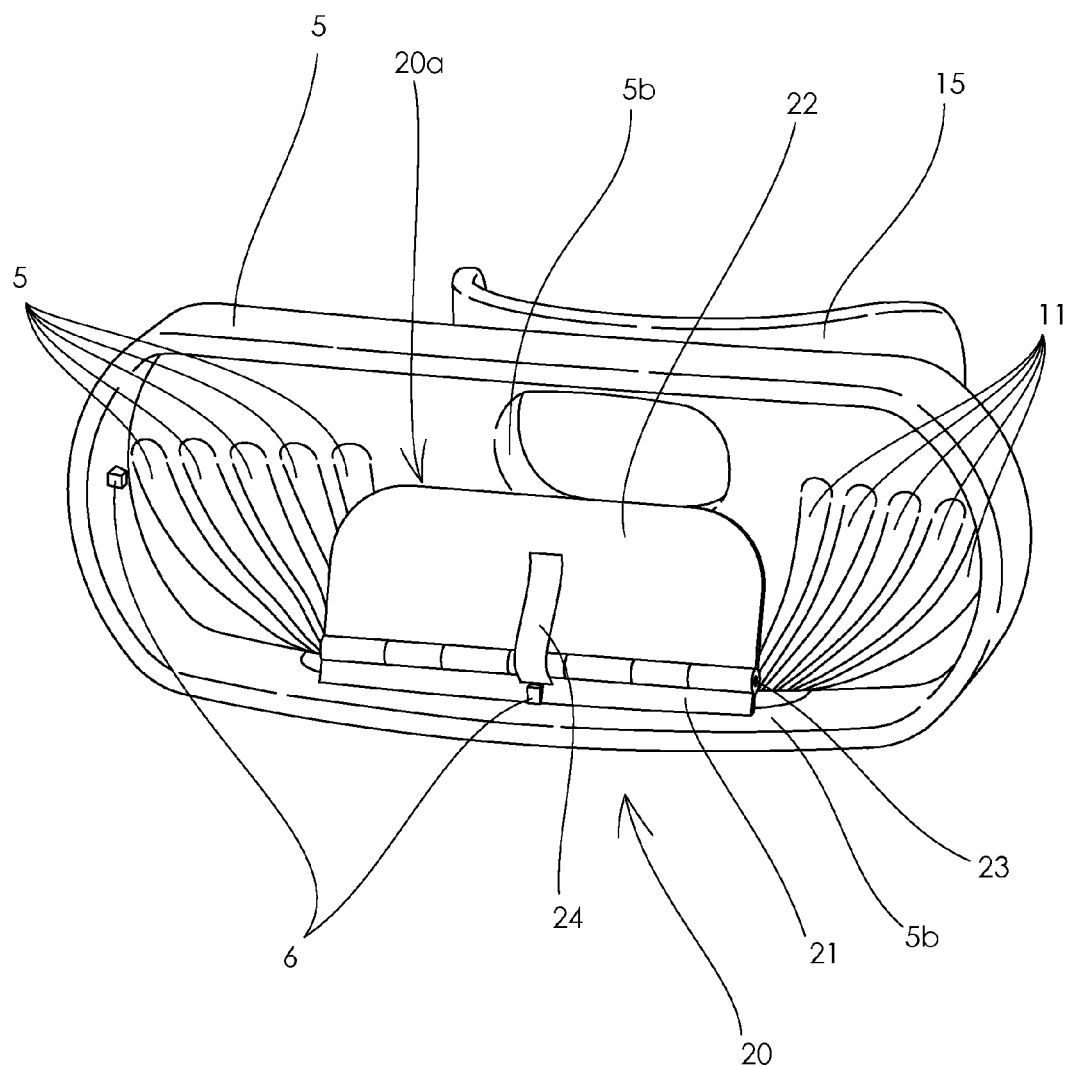
FIG. 10 is a perspective view of a third embodiment of the present invention shown without the filter.

FIG. 10 is a perspective view of a third embodiment of the present invention shown without the filter, in this embodiment 20, the fluid deflector 20a is on a hinge that allows the fluid deflector to rotate upward and downward. Specifically, the fluid deflector 20a comprises a hinge base wing 21, a hinge deflector wing 22, a hinge pivot pin 23, and a hinge spring 24. The hinge spring 24 maintains the fluid deflector in the position shown in FIG. 10C at rest phase (during neither inhalation nor exhalation).

Figure 10A:
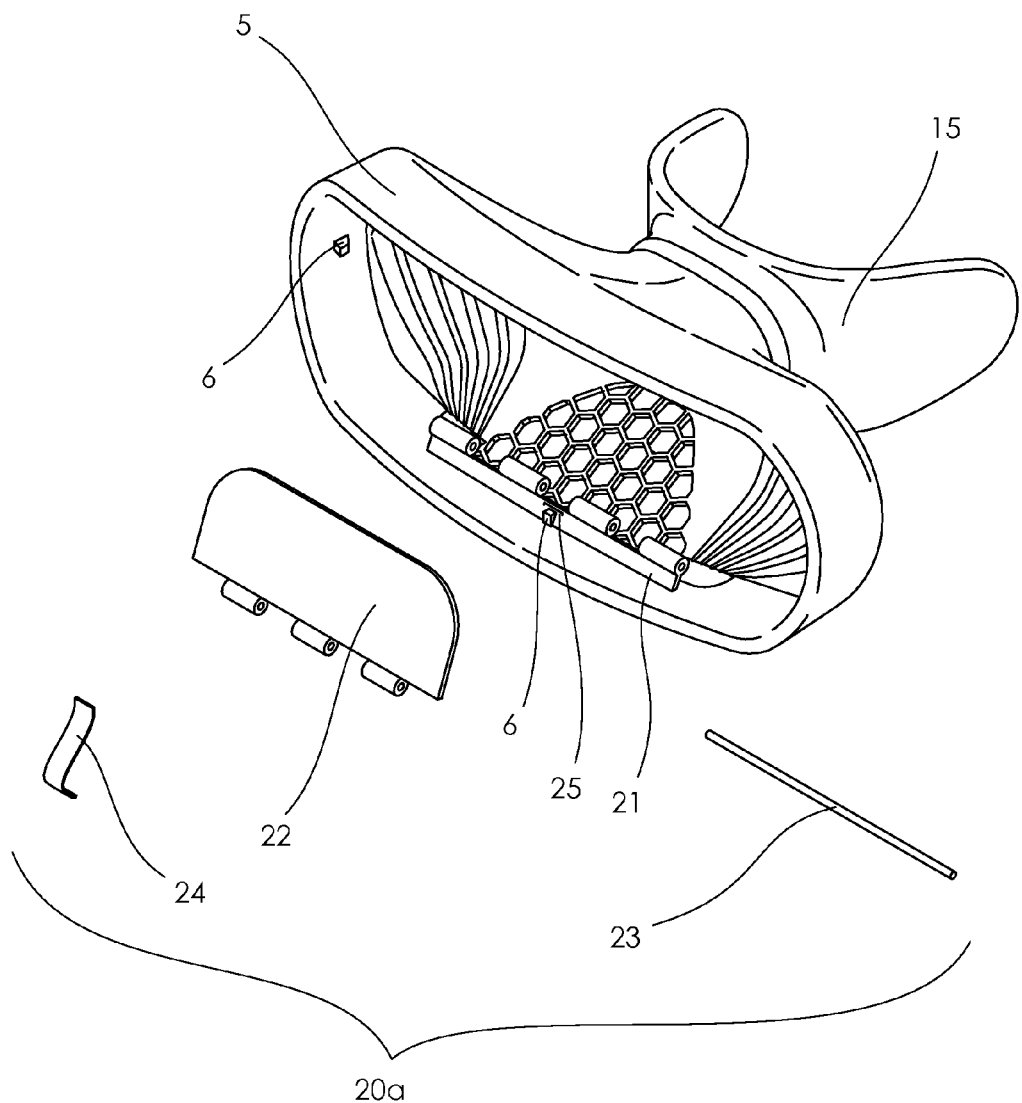
FIG. 10A is an exploded view of the embodiment shown in FIG. 10.
Figure 10:
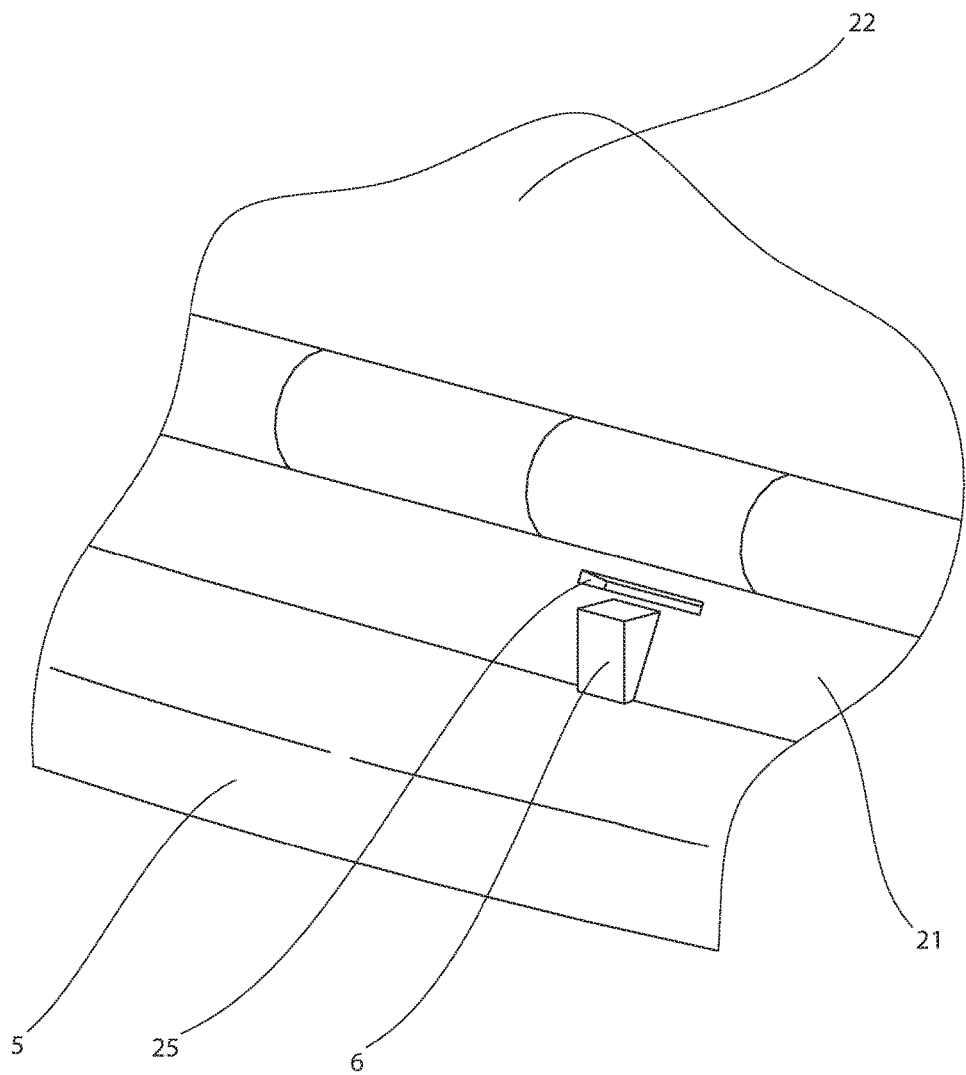
Figure 10C:
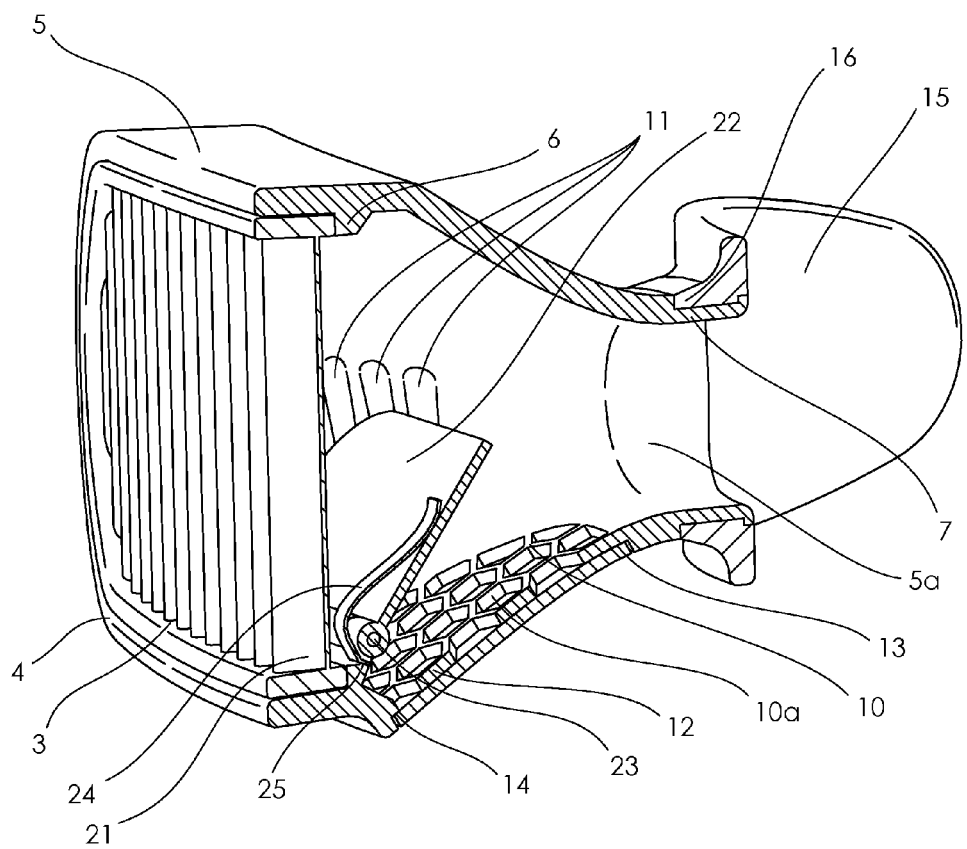
FIG. 10C is a side cross-section view of a third embodiment of the present invention with the spring shown in a neutral state.

FIG. 10A is an exploded view of the embodiment shown in FIG. 10, and FIG. 10B is a detail view of the spring attachment slot. These two figures show how the fluid deflector 20a is assembled. The lower end of the hinge spring 24 fits into the spring attachment slot 25.

Figure 11:
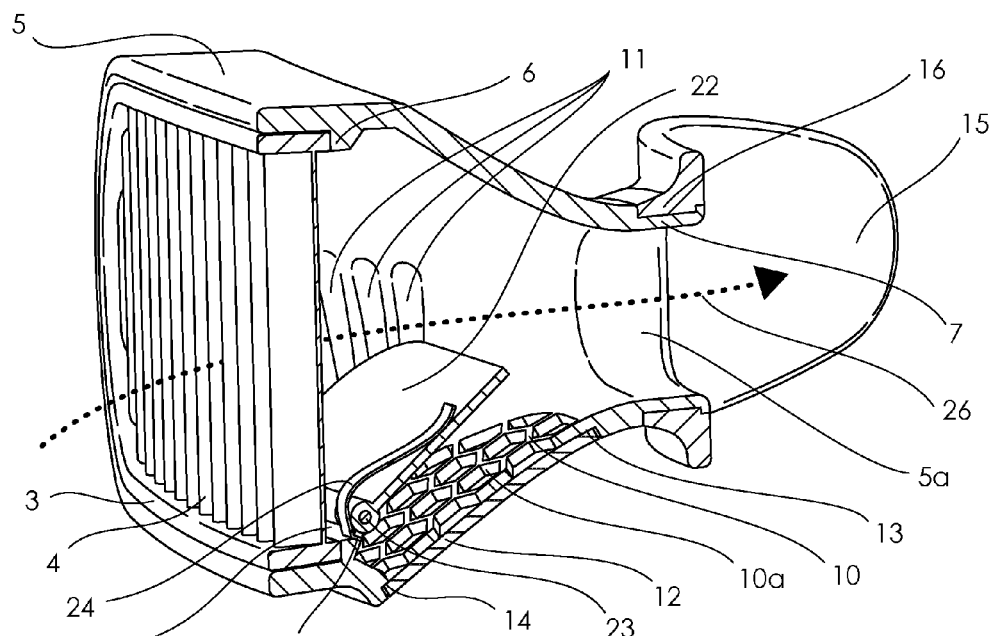
FIG. 11 is a side cross-section view of a third embodiment of the present invention shown in an inhalation state.
Figure 12:
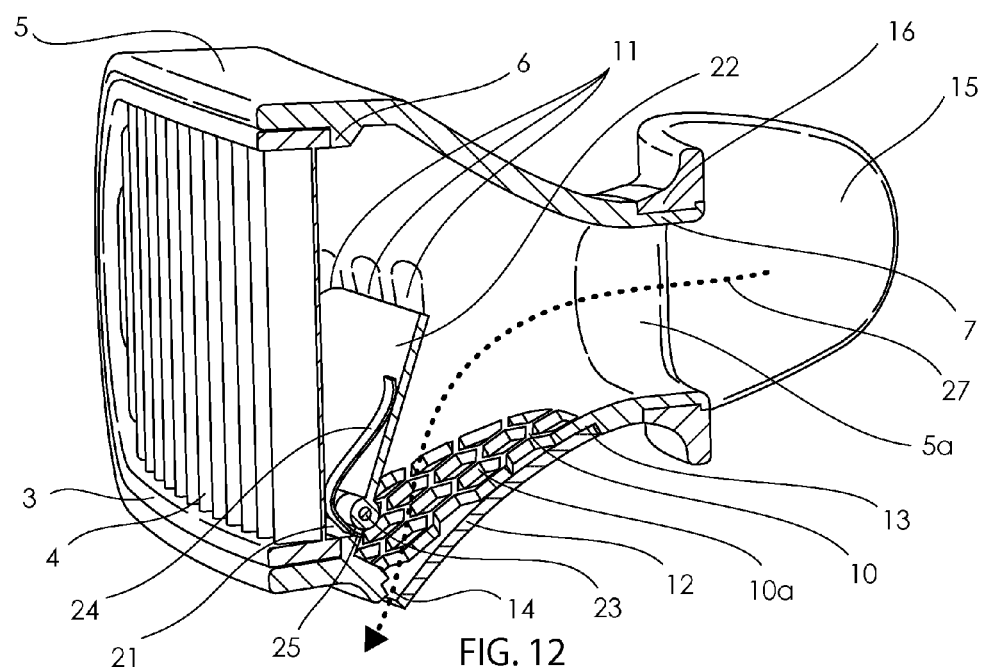
FIG. 12 is a side cross-section view of a third embodiment of the present invention shown in an exhalation state.

FIG. 11 is a side cross-section view of a third embodiment of the present invention shown in an inhalation state, and FIG. 12 is a side cross-section view of a third embodiment of the present invention shown in an exhalation state. As shown in these figures, the fluid defector 20a flexes downward during inhalation and upward during exhalation. The function of the fluid deflector 12 in the two alternate embodiments is the same as described above for the first embodiment. Because the fluid deflector 20a is allowed to move in this embodiment, it is likely more effective than the first embodiment, for the same reasons discussed above relative to the second embodiment. (Note that herein, the "second embodiment" is also referred to as the "first alternate embodiment" and the "third embodiment" is also referred to as the "second alternate embodiment.") In all three embodiments, the fluid deflector 8, 18, 20a has a front-facing arcuate surface and a rear-facing concave surface.

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A fluid management device comprising:
   (a) an air filter assembly comprising a filter, a body, a mouthpiece and a flap valve; and
   (b) a fluid deflector situated between the filter and the mouthpiece;
   wherein the body comprises fluid collection guide channels located on an inside surface of the body behind the fluid deflector;
   wherein the fluid collection guide channels direct condensation and saliva into a collection basin located behind the fluid deflector at a base or the fluid deflector;
   wherein the flap valve comprises a first end and a second end, the first end being attached to the body, and the second end being situated directly beneath the collection basin; and
   wherein when the flap valve is in an open position, it allows fluids collected in the collection basin to escape from the device by dripping out of it.

2. The fluid management device of claim 1, wherein the body comprises a filter orifice situated on a front side of the body, the filter comprises filter media and a frame, and the frame fits inside of the filter orifice.

3. The fluid management device of claim 2, wherein the filter orifice comprises at least one filter positive stop on an interior of the filter orifice, and wherein the filter positive stop prevents the filter front coming into contact with the fluid deflector.

4. The fluid management device of claim 1, wherein the fluid deflector comprises a filter positive stop on a front surface of the fluid deflector, and wherein the filter positive stop prevents the filter from coming into contact with the fluid deflector.

5. The fluid management device of claim 1, wherein the fluid deflector is a rigid and stationary plastic shield that is fixedly attached to a bottom of the filter orifice.

6. The fluid management device of claim 1, wherein the fluid deflector is comprised of a flexible material that allows the fluid deflector to flex downward during inhalation and upward during exhalation.

7. The fluid management device of claim 1, wherein the fluid deflector comprises a hinge spring that allows the fluid deflector to flex downward during inhalation and upward during exhalation.

8. The fluid management device of claim 1, further comprising a flap valve support structure that is integral to the body and that lies between the flap valve and the fluid deflector.

9. The fluid management device of claim 8, wherein the fluid collection guide channels are located on either side of the flap valve support structure.

10. The fluid management device of claim 1, wherein the fluid deflector comprises a front-facing convex surface and a rear-facing concave surface.

* * * * *